(12) United States Patent
McMurray (10) Patent No.: US 8,631,795 B1
(45) Date of Patent: Jan. 21, 2014

(54) ENHANCED AIRWAY

(75) Inventor: Roxanne R. McMurray, Shoreview, MN (US)

(73) Assignee: Roxanne R. McMurray, Shoreview, MN (US)

( * ) Notice: Subject to any disclaimer, the term of this patent is extended or adjusted under 35 U.S.C. 154(b) by 306 days.

(21) Appl. No.: 13/102,725

(22) Filed: May 6, 2011

Related U.S. Application Data

(60) Provisional application No. 61/370,695, filed on Aug. 4, 2010.

(51) Int. Cl.
*A61M 11/00* (2006.01)

(52) U.S. Cl.
USPC .................................. 128/207.14; 128/207.15

(58) Field of Classification Search
USPC ........................................ 128/207.14, 207.15
See application file for complete search history.

(56) References Cited

U.S. PATENT DOCUMENTS

| | | | |
|---|---|---|---|
| 4,338,930 A | | 7/1982 | Williams |
| 4,821,715 A | | 4/1989 | Downing |
| 5,054,482 A | * | 10/1991 | Bales ........................ 128/207.14 |
| 5,060,647 A | * | 10/1991 | Alessi ....................... 128/207.14 |
| 5,259,376 A | * | 11/1993 | Bales ........................ 128/207.17 |
| D348,099 S | * | 6/1994 | Terrian ......................... D24/108 |
| 5,318,017 A | * | 6/1994 | Ellison ..................... 128/200.24 |
| 5,333,608 A | * | 8/1994 | Cummins ................ 128/207.14 |
| 5,590,643 A | * | 1/1997 | Flam ........................ 128/200.26 |
| 5,743,258 A | | 4/1998 | Sato et al. |
| 5,937,858 A | | 8/1999 | Connell |
| 6,162,206 A | * | 12/2000 | Bindokas et al. ............. 604/533 |
| 6,830,049 B2 | | 12/2004 | Augustine et al. |
| 7,171,962 B1 | | 2/2007 | Bloem |
| 2004/0194785 A1 | | 10/2004 | Miller |

OTHER PUBLICATIONS

Bay Medical, Oral Airways Catalog, published at least as early as Apr. 2010 (6 pages).
Wikipedia, Thermoplastic Elastomer, http://en.wikipedia.org/wiki/Thermoplastic_elastomer, published at least as early as May 10, 2010, (4 pages).
Orsupply.com, Rusch Nasopharyngeal Disposable Robertazzi Mediprene Airways, http://www.orsupply.com/product/Rusch-Nasopharyngeal-Disposable-Robertazzi-Mediprene-Airways-Box-of-/3837/brand/Rusch/114, published at least as early as May 10, 2010, (2 pages).

(Continued)

*Primary Examiner* — Steven Douglas
(74) *Attorney, Agent, or Firm* — Michael Best & Friedrich LLP (57) ABSTRACT

An enhanced airway for creating an airway in a patient including a rigid connector with an insertion portion inserted into a flexible tube, and a padding member surrounding the flexible tube and the inserted portion of the rigid connector. The rigid connector includes a circuit end that may be directly coupled to an anesthesia circuit, reducing risk of fire caused by diffusing oxygen. The circuit end may also be covered by an oxygen mask or left open and uncoupled. The flexible tube enables a comfortable and less-injury prone creation of an airway in the patient's oral cavity. The rigid connector prevents a patient from biting down and collapsing the flexible tube and, if also inserted in the patient's airway, an endotracheal tube or a laryngeal mask airway. The padding member cushions the rigid connector, preventing damage and injury to a patient's teeth upon biting the rigid connector.

16 Claims, 10 Drawing Sheets

(56) References Cited

OTHER PUBLICATIONS

Mediprene, Thermoplastic Elastomers for Medical Applications, http://www.elastotpe.com/en/products_mediprene.html, published at least as early as May 10, 2010, (1 page).

Matweb, Vita Thermoplastic Polymers Mediprene, http://www.matweb.com/search/DataSheet.aspx?MatGUID=5372214a804f46c888ae36e53500fa77&ckck=1, published at least as early as May 10, 2010, (1 page).

* cited by examiner

ENHANCED AIRWAY

RELATED APPLICATIONS

This patent application claims priority to U.S. Provisional Patent Application Ser. No. 61/370,695, filed Aug. 4, 2010, the entire contents of which are herein incorporated by reference.

FIELD OF INVENTION

Embodiments of the invention are directed to devices and related methods used to create airways in patients.

BACKGROUND

An oropharyngeal airway (OPA), also referred to as an oral airway, is used to create an air passageway between the mouth and the posterior pharyngeal wall of a patient. Unconscious patients (e.g., under general anesthesia) and heavily sedated semi-unconscious patients (e.g., under monitored anesthesia care (MAC)) may have an oral airway inserted to relieve an obstructed airflow.

Prior art oral airways include a hard curved piece of plastic that is often poorly tolerated in conscious and semi-conscious patients. For instance, these rigid oral airways may induce gagging, vomiting, aspiration, layrngospasm, damage to teeth (due to patient biting), and damage to lips. If such an oral airway is left in place for a prolonged period of time, sores can develop in the mouth and bleeding may occur. Improper sizing of these oral airways introduces problems as well. Given the rigid nature of oral airways, sizing must be done without error. A rigid oral airway that is too large can close the glottis and cut off an air supply. A rigid oral airway that is too small can cause tongue sores and swelling.

Endotracheal tubes (ETT) are flexible and inserted beyond the vocal cords into the trachea, which is further into the oral passageway than an oral airway. ETTs are somewhat flexible and compressible and include an inflatable portion which causes a seal in the airway and secures the ETT in place. The flexible and compressible nature of an ETT enables a patient to collapse the ETT by biting, which can cut off an air supply and lead to pulmonary edema.

Nasopharyngeal airways, also referred to as nasal airways, are also used to alleviate airway obstructions, but create an air passageway between the nose and posterior pharyngeal wall of a patient. Nasal airways may also cause discomfort and injury to a patient. For instance, nasal airways may cause nosebleeds and local nasal discomfort.

SUMMARY

In one embodiment, the invention provides an enhanced airway apparatus. The enhanced airway includes a tubular member made of a flexible thermoplastic elastomer material (e.g., mediprene) and including a first inner diameter. The tubular member includes a first end and a beveled end. The enhanced airway further includes a connector and a padding member with a tubular shape. The connector includes an insertion portion with a first diameter and a connecting portion. The first end of the tubular member is received by the padding member to form a padded tubular portion and the padded tubular portion receives the insertion portion of the connector. The connecting portion has a larger diameter than the first diameter and is configured to be coupled to an anesthesia breathing circuit. The connector insertion portion is generally sized to extend beyond the patient's incisors and the tubular member is generally sized to extend into the oral cavity, but not beyond the epiglottis of the patient. In some embodiments, the connector is rigid such that the connector prevents collapse of the enhanced airway due to patient biting.

In another embodiment, the invention provides a method of creating an airway in a patient by inserting an enhanced airway apparatus as described above into a patient's nasal or oral cavity. Additionally, in some embodiments, after insertion of the enhanced airway into the patient, the method further includes 1) placing an oxygen mask over the patient's nose and mouth and the connecting portion, 2) coupling an anesthesia breathing circuit to the connecting portion, or 3) inserting an ETT or laryngeal mask airway (LMA) alongside the inserted enhanced airway, the connector insertion portion preventing the collapse of the enhanced airway, ETT, and/or LMA due to patient biting.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

FIGS. 1A-B, 2, and 3 depict an enhanced airway 100 according to embodiments of the invention. The enhanced airway 100 includes a connector 105, a wrap 110, and a tube 115, which form an airway 117. The connector 105 is a rigid, generally inflexible body with a circuit end 120, a separation plate 125, and an insertion end 130. The insertion end 130 is hidden by the wrap 110 in FIGS. 1A-1B. The connector 105 is, for instance, made of a hard plastic material such as polyethylene. The circuit end 120 has an approximately 15 mm outer diameter and is operable to be directly coupled to an anesthesia circuit and an ambu bag (see, e.g., FIGS. 11 and 12, respectively). In some uses, however, the circuit end 120 is not directly coupled to an anesthesia circuit or an ambu bag, but, rather, is used with an oxygen mask that covers the patient's mouth, nose, and the circuit end 120 (see, e.g., FIG. 13). An oxygen mask is of particular use for semi-conscious patients, although the oxygen mask is also used in other patient scenarios.

Figure 4A:
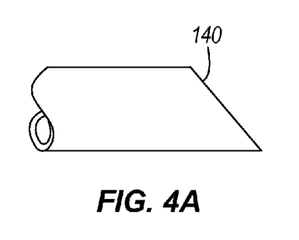
FIGS. 4A-C depict the beveled end of the insertion end of the enhanced airway tube.
Figure 4B:
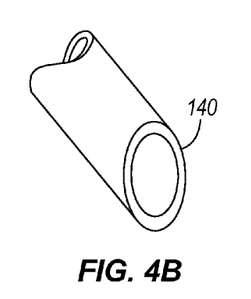
Figure 4C:
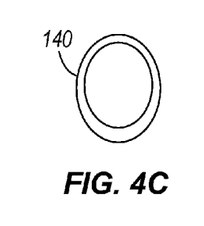
Figure 5:
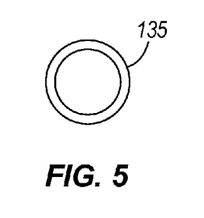
FIG. 5 depicts a connector receiving end of the enhanced airway tube.
Figure 6:
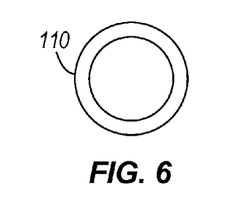
FIG. 6 depicts one end of a gel wrap that is placed over the connector receiving end of the enhanced airway tube.
Figure 7:
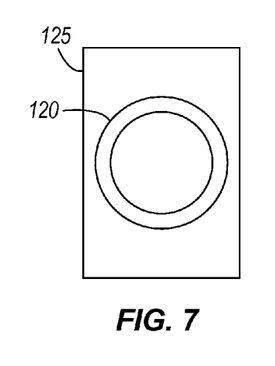
FIG. 7 depicts a circuit end of the connector that may be coupled to an external anesthesia device.
Figure 8:
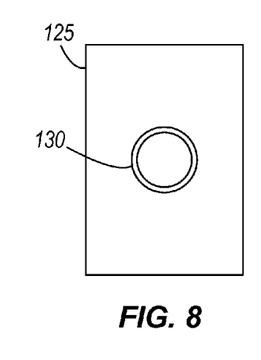
FIG. 8 depicts the insertion end of the connector that is inserted into the connector receiving end of the enhanced airway tube.

The tube 115 is a flexible and compressible tube made of, for instance, a latex free, soft thermoplastic elastomer, such as mediprene. The insertion end 130 of the connector 105 is received by a connector receiving end 135 of the tube 115. The insertion end 130 of the connector 105 and the connector receiving end 135 of tube 115 are friction fitted such that, once inserted, the connector 105 is secured within the tube 115 by friction. The friction forces are increased by the elastic forces of the tube 115 compressing inward onto the insertion end 130 of the connector 105. The outer diameter of the insertion end 130 is approximately equal to or slightly greater than the inner diameter of the tube 115 to ensure a snug fit. As depicted in FIGS. 4A-C, the insertion end 140 of the tube 115 includes a beveled tip for comfort and gentle insertion into a patient's airway. The connector receiving end 135 of the tube 115 has a flat, non-beveled tip, as depicted in FIG. 5. The connector receiving end 135 is pushed onto the insertion end 130 of the connector 105. In some instances, the connector receiving end 135 is pushed onto the insertion end 130 of the connector 105 until reaching the separation plate 125. In some embodiments, the connector receiving end 135 flares out (a "trumpet style") to ease insertion of the insertion end 130 of the connector 105 into the tube 115.

The wrap 110 is positioned around the tube 115 (i.e., the tube 115 is inserted into the wrap 110). The wrap 110 is made of a soft material to provide cushioning or padding for the rigid connector 105. The cushioning prevents harm to teeth of a patient that bites on the enhanced airway 100. The wrap is made of a gel-like nylon material and is sized to fit tightly onto the tube 115 to prevent slippage. In some embodiments with a flared connector receiving end 135, the wrap 110 also includes a flared end. In other embodiments with a flared connector receiving end 135, the wrap 110 is reduced in size so as not to cover the flared portion of the tube 115. In some embodiments, the wrap 110 is sized to fit tightly over the connector 105, and the connector 105 fits tightly over the tube 115.

Figure 9A:
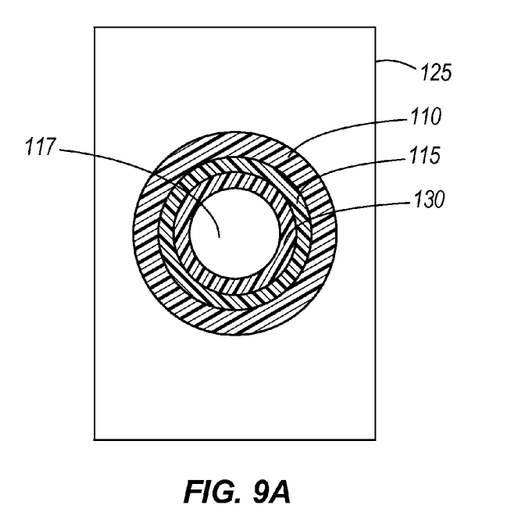
FIG. 9A depicts a cross section of the enhanced airway along line A of FIG. 2.
Figure 9B:
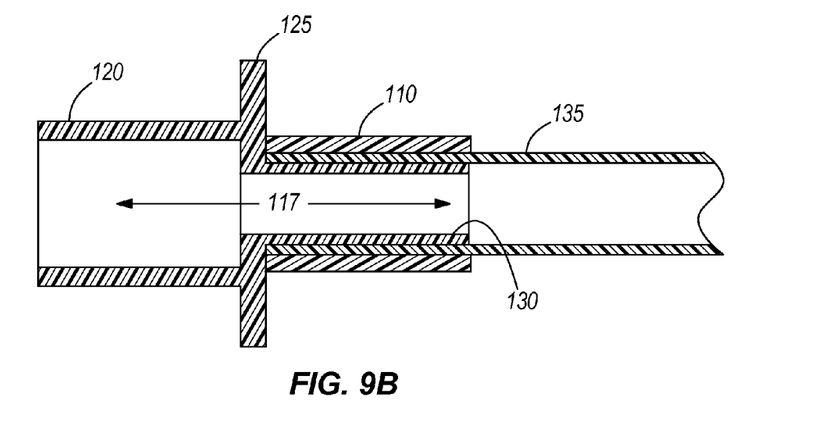
FIG. 9B depicts a cross section of the enhanced airway along line B of FIG. 2.

Cross sections of the enhanced airway 100 are depicted in FIGS. 9A and 9B, which illustrates that the airway 117 is surrounded first by the insertion end 130 of the connector 105, then the tube 115, and finally the wrap 110.

The tube 115 is designed in several sizes to accommodate the various pharynx sizes of patients. Below is an exemplary size chart for the tube 115 and connector 105 based on estimated pharynx sizes by patient age. The size, length and diameter of the enhanced airway 100 are merely exemplary and should not be interpreted as limiting.

| Patient Age | Tube 115 Length (mm) | Tube 115 Internal Diameter (mm) | Tube 115 External Diameter (mm) | Total Connector 105 Length (mm) | Insertion End 130 Length (of Connector 105) (mm) |
|---|---|---|---|---|---|
| 0-6 mo | 70 | 3.2 | 6.7 | 34 | 22 |
| 6 mo-1 yr | 80 | 3.9 | 7.4 | 35 | 22 |
| 1-4 yr | 90 | 4.5 | 8.0 | 36 | 24 |
| 5-8 yr | 100 | 5.2 | 8.7 | 36 | 24 |
| 8-10 yr | 110 | 5.9 | 9.4 | 38 | 28 |
| Adult female | 130 | 6.5 | 10 | 40 | 30 |
| Adult large male | 150 | 7.4 | 10.7 | 40 | 30 |

Figure 10:
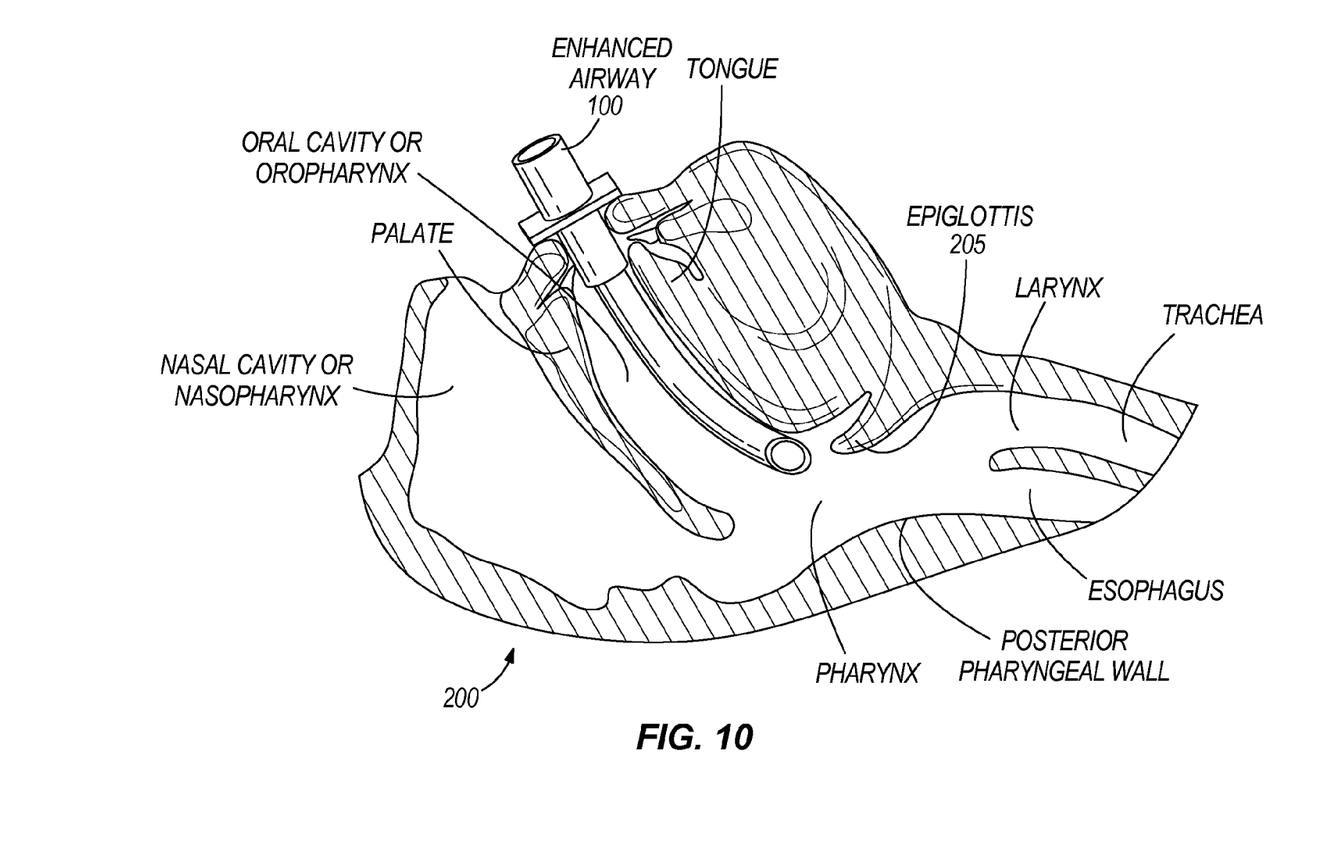
FIG. 10 depicts the enhanced airway positioned in the pharynx of a patient.

FIG. 10 depicts the enhanced airway 100 inserted into the pharynx of a patient 200. In contrast to an LMA and ETT (see, e.g., FIGS. 13A and 14A, respectively), the enhanced airway does not extend beyond the epiglottis 205 of the patient. The separation plate 125 prevents the enhanced airway from entering the oral cavity and provides a surface to ensure that the insertion end 130 of the connector 105 is not over-extended into the tube 115.

Figure 1A:
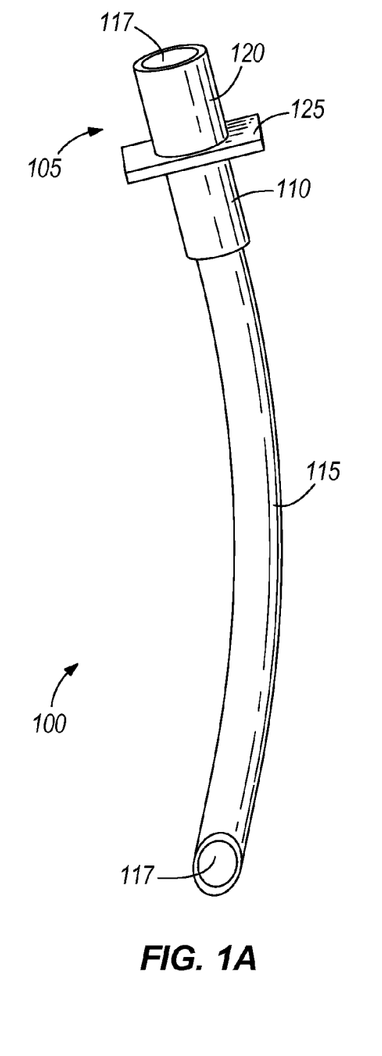
FIGS. 1A and 1B depict a top view and side view of an enhanced airway, respectively.
Figure 1B:
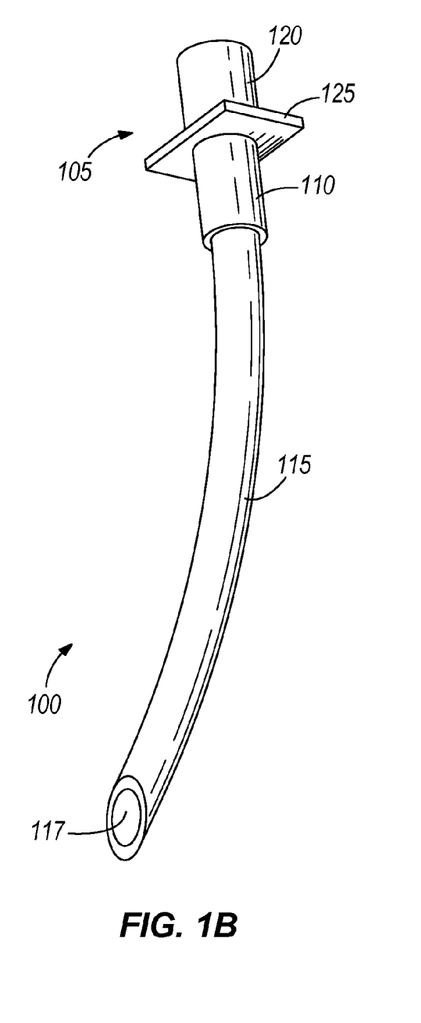
Figure 2:
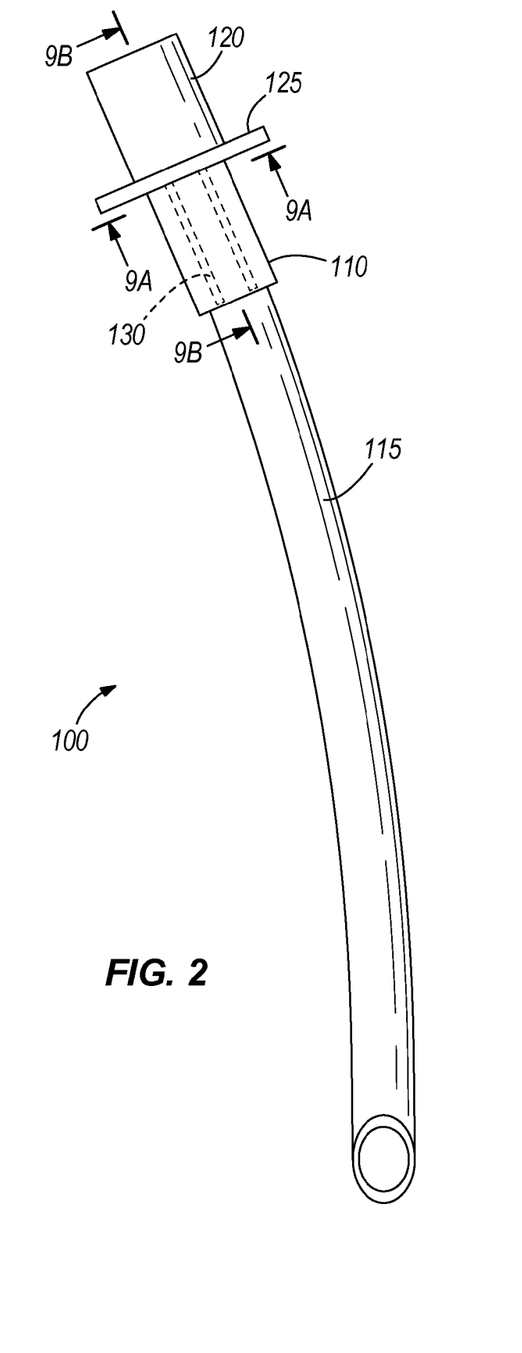
FIG. 2 depicts another top view of the enhanced airway.
Figure 3:
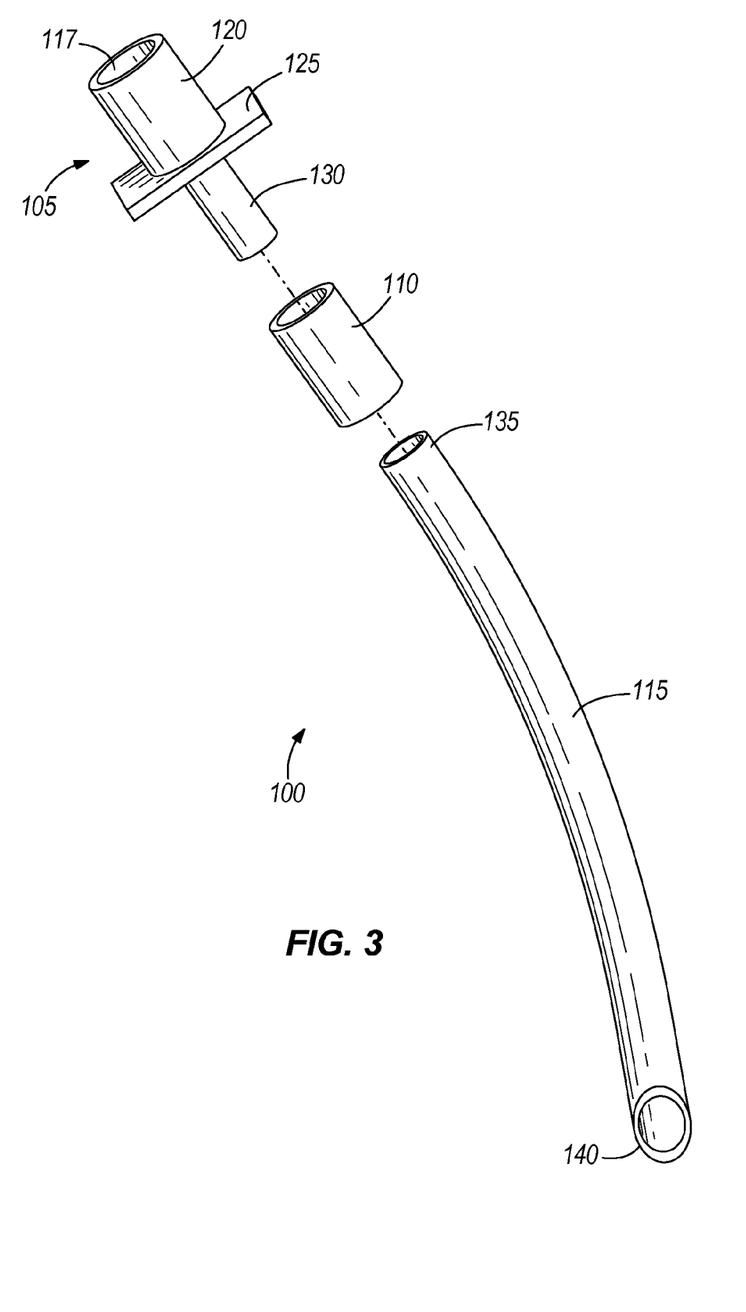
FIG. 3 depicts an exploded view of the enhanced airway.
Figure 11:
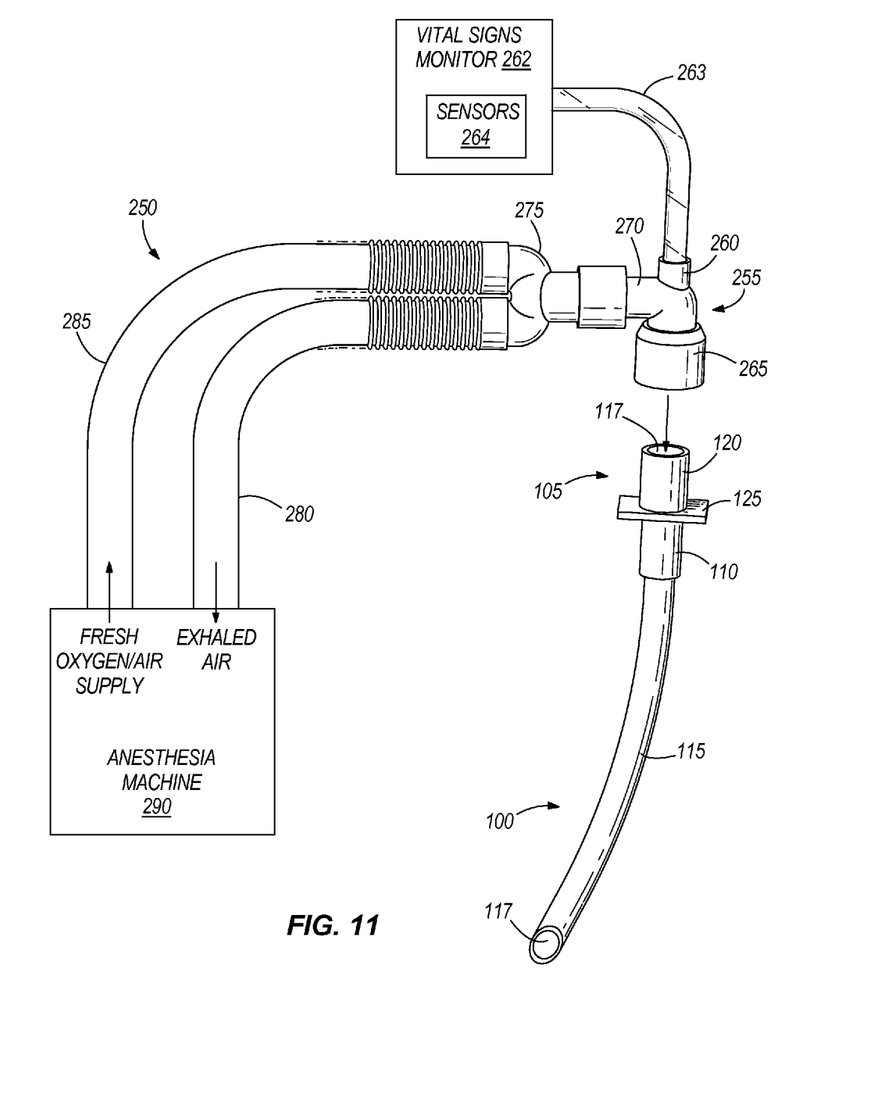
FIG. 11 depicts the enhanced airway coupled to an anesthesia circuit.

Generally, the enhanced airway 100 is provided to health care facilities fully assembled (e.g., as in FIG. 1) and is individually wrapped to be a single use (i.e., disposable) device. A medical practitioner determines the properly sized enhanced airway 100 for the patient 200, removes the enhanced airway 100 from its packaging, and inserts the enhanced airway 100 into a patient 200. The inserted enhanced airway 100 forms an airway from the mouth to just before the epiglottis 205 (in the vallecula) of the patient 200. In some embodiments, the circuit end 120 is coupled to an anesthesia circuit as illustrated in FIG. 11.

The increased flexibility, reduced diameter, and increased length of the enhanced airway 100 each provide benefits over traditional oral airways. The tube 115 of the enhanced airway 100 is softer and more flexible than traditional oral airways, which eliminates the issues associated therewith. For instance, the tube 115 will reduce gagging, vomiting, aspiration, laryngospasm, and damage to teeth relative to the traditional oral airway. Furthermore, choosing the appropriate size of the enhanced airway 100 is easier than traditional oral airways as improper sizing of the enhanced airway 100 has less potential to harm a patient by, e.g., closing the glottis and causing tongue sores, swelling, and bleeding. Additionally, the enhanced airway 100 is easier to insert, as the flexibility prevents pushing the tongue backward, which can block the airway. Unlike the traditional oral airway, the enhanced airway 100 may be inserted without the use of a tongue depressor and without the need to rotate the device 180 degrees before passing over the tongue, thus simplifying insertion. The use of a rigid connector 105 within the flexible tube 115 prevents a patient from biting down and closing off the airway 117. The wrap 110 provides cushioning to prevent a patient that bites on the connector 105 from harming his or her teeth. Both the wrap 110 and insertion end 130 of the connector 105 are generally sized to extend beyond the incisors of the patient 200.

The enhanced airway 100 also reduces safety issues related to the use of oxygen generating devices in connection with oral airways. When medical oxygen is used for a patient, a potential fire hazard is created by the flammable oxygen diffusing in the environment near the patient. Traditional oral airways are an open system and cannot be directly coupled to a circuit (e.g., an oxygen generating anesthesia circuit). Therefore, certain procedures with instruments that pose a fire/spark risk (e.g., procedures including cautery), particularly near a patient's face, pose a fire hazard for the patient and the staff when using a traditional oral airway. The enhanced airway 100 is directly coupled to a circuit, which diminishes oxygen diffusion and the associated fire hazard in the area near the patient's face. The circuit also allows for medical air to be administered, decreasing FiO2 (oxygen concentration) to safe levels. This decrease results in increased safety for both the patient 200 and medical staff. Furthermore, a circuit is operable to measure FiO2 and, therefore, the use of a circuit with the enhanced airway 100 enables more accurate measuring of FiO2 at the oxygen source. Measuring FiO2 at the source allows safety issues to be more accurately assessed and controlled to various levels. Additionally, use of the circuit with the enhanced airway 100 enables safe delivery of a higher concentration and/or higher amount of oxygen to the patient 200 than otherwise possible (e.g., up to a 100% level FiO2).

The enhanced airway 100 is usable in various medical situations, including during MAC (patient is semi-conscious), sedation-free situations, and general anesthesia (patient is unconscious). For instance, during MAC, the enhanced airway 100 may be coupled to an anesthesia circuit (see FIG. 11), used with an oxygen mask (not directly coupled) (see FIG. 12), or not coupled to another device (FIG. 10).

FIG. 11 depicts the enhanced airway 100 coupled via connector 105 to an anesthesia circuit 250. The anesthesia circuit 250 includes a circuit connector 255 with three openings: a first opening 260 for coupling the circuit connector 255 to a vital signs monitor 262; a second opening 265 for coupling to the circuit end 120; and a third opening 270 for coupling to a Y-connector 275. The vital signs monitor 262 is coupled to the first opening 260 via a sensor tube 263, which enables sensors 264 to monitor the $FiO_2$ and end-tidal carbon dioxide ($ETCO_2$) levels in the airflow through the circuit connector 255. The vital signs monitor 262 is operable to generate alerts by comparing measured $FiO_2$ and $ETCO_2$ levels to stored thresholds (e.g., thresholds stored in a memory). The Y-connector 275 is coupled to a first circuit tube 280 and a second circuit tube 285. The first and second circuit tubes 280 and 285 are coupled to the anesthesia machine 290. The particular anesthesia circuit 250 is merely exemplary as other types of anesthesia circuits may also be coupled to the circuit end 120.

Figure 12:
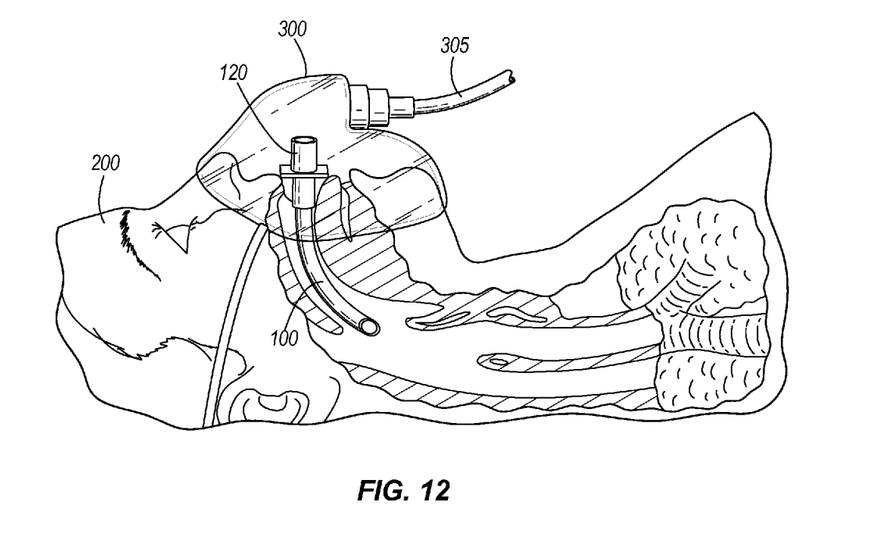
FIG. 12 depicts the enhanced airway in use with an oxygen mask.

FIG. 12 depicts the enhanced airway 100 in use with oxygen mask 300. The mask 300 is placed over the mouth of the patient 200 and the circuit end 120 of the inserted enhanced airway 100. The mask includes an airflow tube 305 that is coupled to, for example, an oxygen supply (not shown), and provides bidirectional airflow.

As shown in FIG. 10, the enhanced airway 100 may also be inserted to create an airway in a patient 200 without coupling the circuit end 120 to another device. For example, the enhanced airway 100 is usable in sedation-free situations and emergencies, such as while a patient is receiving cardiopulmonary resuscitation (CPR), without connecting the circuit end 120 to an anesthesia circuit.

Figure 13A:
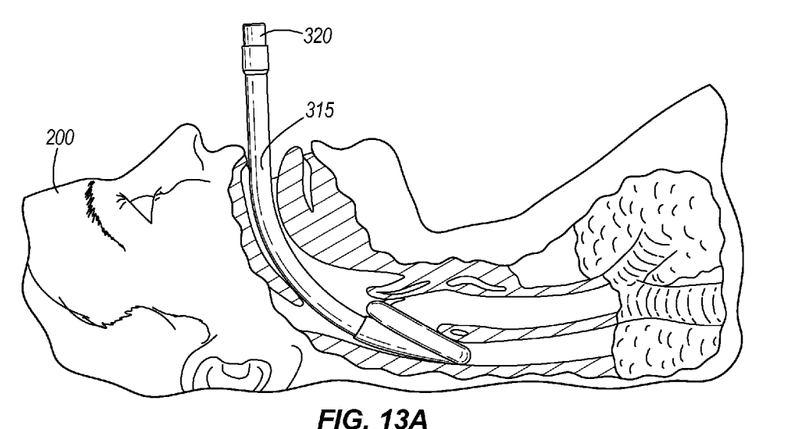
FIGS. 13A-B depict the enhanced airway in use with an LMA.
Figure 13B:
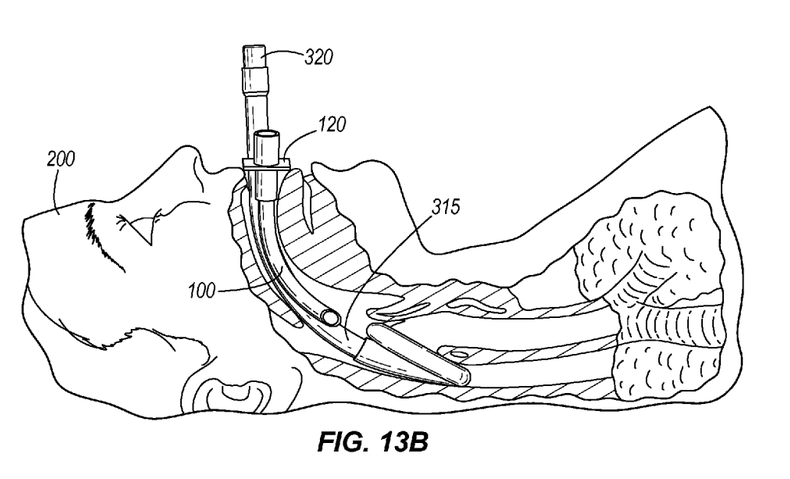

During general anesthesia, an ETT or LMA may be inserted into the patient's airway for supplying oxygen to the patient and to assist in ventilating the patient. FIG. 13A depicts an LMA 315 inserted into patient 200. The LMA 315 includes an end connector 320, which may be coupled to an anesthesia circuit, such as anesthesia circuit 250 described above. In FIG. 13B, the enhanced airway 100 is shown inserted alongside the smaller diameter LMA 315. The rigid connector 105 of the enhanced airway 100 prevents the collapse of the LMA 315 from biting by the patient 200. Additionally, the separation plate 125 prevents the enhanced airway 100 from sliding into the patient's oral cavity. As the enhanced airway 100 is positioned within the oral cavity, the tube 115 provides additional stability to prevent movement of the rigid connector 115 within or out of the bite zone of the patient 200.

Figure 14A:
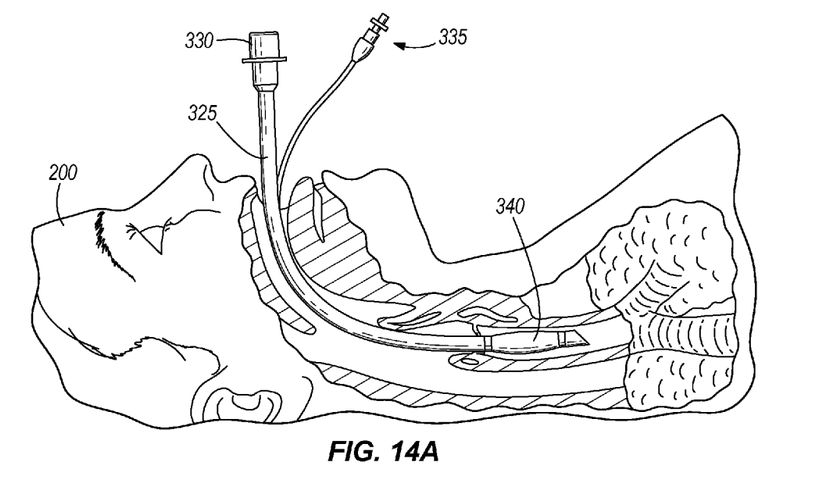
FIGS. 14A-B depict the enhanced airway in use with an ETT.
Figure 14B:
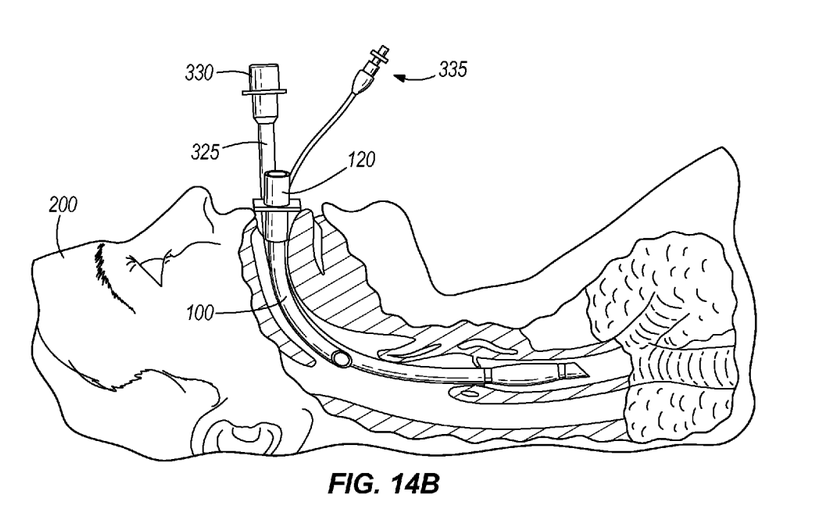

FIG. 14A depicts an ETT 325 inserted into the patient 200. The ETT 325 includes an end connector 330 and air port 335. The end connector 330 may be coupled to an anesthesia circuit, such as anesthesia circuit 250 described above. The air port 335 is used to supply air to inflate a pilot cuff 340 to seal the airflow through the trachea of patient 200 and ensure the ETT 325 stays in the proper position. For removal of the ETT 325, the pilot cuff 340 is deflated via air port 335. In FIG. 14B, the enhanced airway 100 is shown inserted alongside the smaller diameter ETT 325. The rigid connector 105 of the enhanced airway 100 prevents the collapse of the ETT 325 from biting by the patient 200. Additionally, the separation plate 125 prevents the enhanced airway 100 from sliding into the patient's oral cavity. As the enhanced airway 100 is positioned within the oral cavity, the tube 115 provides additional stability to prevent movement of the rigid connector 115 within or out of the bite zone of the patient 200.

In some embodiments, the enhanced airway 100 provides direct access to patient secretions in the upper airway of patients. A flexible suction catheter is inserted through the enhanced airway 100 (through airway 117) to reach the secretions. Suction forces are applied to the non-inserted end of the flexible suction catheter to suction and remove secretions of the patient. Secretion suction enables removal of secretions in the upper airway of patients, which is particularly beneficial for those patients unable to cough and/or clear their own secretions effectively. The enhanced airway 100 reduces the trauma caused to the oral muscosa by a flexible suction catheter that would otherwise be present without the use of the enhanced airway.

In some embodiments, the enhanced airway 100 is inserted into the nasal cavity of the patient 200 to create an airway. In some instances, the enhanced airway 100 is used eliminate obstructions in the upper airway, such as caused by sleep apnea. Additionally, the enhanced airway 100 will reduce or eliminate snoring when worn by a sleeping patient. In some embodiments, the enhanced airway 100 is used to create airways in animals in veterinary applications.

Thus, the invention provides, among other things, an enhanced airway to provide a safe, comfortable airway in a patient. Various features and advantages of the invention are set forth in the following claims.

What is claimed is:

1. An oral airway apparatus for creating an oral airway in a patient having an epiglottis, the apparatus comprising:
   a padding member having a cylindrical cavity;
   a flexible tubular member having a length between about 70 mm and 150 mm, including
      a first end positioned within the cylindrical cavity of the padding member, and
      a beveled end for insertion into an oral airway of the patient, wherein the flexible tubular member is sized such that the beveled end does not extend past the epiglottis; and
   a connector including
      an insertion portion positioned within the first end of the flexible tubular member and within the cylindrical cavity of the padding member, wherein the insertion portion has a first diameter,
      a connecting portion with a larger diameter than the first diameter and configured to be coupled to an anesthesia breathing circuit, and a separation member positioned between the insertion portion and the connecting portion.

2. The oral airway apparatus of claim 1, wherein the connector is made of a rigid material to prevent collapse of the first end of the flexible tubular member due to patient biting.

3. The oral airway apparatus of claim 2, wherein a length of the connector is sized to extend beyond incisors of the patient.

4. The oral airway apparatus of claim 1, wherein the flexible tubular member is made of a thermoplastic elastomer material.

5. The oral airway apparatus of claim 1, further comprising:
   an anesthesia circuit connector coupled to the connecting portion, and
   an anesthesia machine coupled to the anesthesia circuit connector.

6. The oral airway apparatus of claim 1, wherein the padding member and insertion portion each have a length of at least 28 millimeters.

7. A method of creating an airway in the patient comprising inserting the oral airway apparatus according to claim 1 into an oral pharynx of the patient.

8. A method of creating an oral airway in a patient having an epiglottis, the method comprising:
   forming an enhanced oral airway including a rigid connector, a flexible tube, and a padding member by
      inserting a first end of the flexible tube into a cylindrical cavity of the padding member, and
      inserting an insertion portion of the rigid connector into a cylindrical cavity of the first end of the flexible tube, wherein the rigid connector includes a connecting portion opposite the insertion portion and a separation plate positioned between the insertion portion and the connecting portion and wherein the flexible tube includes a beveled end opposite the first end; and
   inserting the enhanced oral airway into an oral cavity of the patient to create the oral airway such that the beveled end does not extend past the epiglottis.

9. The method of claim 8, further comprising coupling an anesthesia circuit to the connecting portion.

10. The method of claim 8, further comprising coupling an anesthesia circuit to the connecting portion and controlling a supply of oxygen to have an FiO2 level within a range of approximately 21% to 100%.

11. The method of claim 8, further comprising coupling the connecting portion to an anesthesia breathing circuit to provide oxygen to the oral airway of the patient and to substantially prevent diffusion of oxygen provided by the anesthesia circuit to an area external to the oral airway of the patient.

12. The method of claim 8, further comprising placing an oxygen mask over a nose and mouth of the patient, as well as over the connecting portion of the inserted enhanced oral airway.

13. The method of claim 8, wherein the connector is made of a rigid material to prevent collapse of the first end of the flexible tube due to patient biting.

14. The method of claim 8, further comprising inserting one of an endotracheal tube and a laryngeal mask airway alongside the enhanced airway, wherein a diameter of the one of the endotracheal tube and the laryngeal mask airway is smaller than a diameter of the insertion portion of the rigid connector such that the insertion portion prevents collapse of the one of the endotracheal tube and the laryngeal mask airway due to patient biting after insertion.

15. The method of claim 8, further comprising inserting a suction catheter through the flexible tube and suctioning secretions of the patient.

16. An oral airway apparatus for creating an oral airway in a patient having an epiglottis, the apparatus comprising:
   a padding member having a cylindrical cavity;
   a flexible tubular member having a length between about 70 mm and 150 mm, including
      a first end positioned within the cylindrical cavity of the padding member, and
      a beveled end for insertion into an oral airway of a patient, wherein the flexible tubular member is sized such that the beveled end does not extend past the epiglottis; and
   a connector including an insertion portion positioned within the first end of the flexible tubular member, the insertion portion made of a rigid material to prevent collapse of the first end of the flexible tubular member due to patient biting.

* * * * *